United States Patent [19]

Horand

[11] Patent Number: 4,580,438

[45] Date of Patent: Apr. 8, 1986

[54] METHOD AND APPARATUS FOR TESTING THE DUPLICATING CHARACTERISTICS OF PRESSURE-SENSITIVE DUPLICATING SHEETS

[75] Inventor: Dieter Horand, Grefrath, Fed. Rep. of Germany

[73] Assignee: Feldmühle Aktiengesellschaft, Düsseldorf, Fed. Rep. of Germany

[21] Appl. No.: 597,470

[22] Filed: Apr. 5, 1984

[30] Foreign Application Priority Data

Apr. 9, 1983 [DE] Fed. Rep. of Germany ....... 3312749

[51] Int. Cl.⁴ ............................................... G01N 3/08
[52] U.S. Cl. ...................................... 73/14; 73/150 R
[58] Field of Search .................. 73/14, 856, 104, 159, 73/150 R

[56] References Cited

U.S. PATENT DOCUMENTS 2,300,107 10/1942 Curado et al. .................... 73/150 R
4,203,320 5/1980 Walter ............................. 73/150 R

FOREIGN PATENT DOCUMENTS 0802870 2/1981 U.S.S.R. .................................. 73/14

Primary Examiner—Donald O. Woodiel
Attorney, Agent, or Firm—Toren, McGeady, Stanger, Goldberg & Kiel

[57] ABSTRACT

In a method and apparatus for testing the duplicating characteristics of pressure-sensitive duplicating sheets and duplicating sets produced therefrom, a stroke grid is drawn on the duplicating sheets to be tested by means of a marking stylus which is actuated either by mechanical or electromechanical devices to apply a selective a contact force, with the grid being evaluated either visually or by photoelectric reflectance measurement, the stroke grid consisting essentially of a plurality of individual strokes which overlap or are closely adjacent but which do not intersect.

14 Claims, 2 Drawing Figures

METHOD AND APPARATUS FOR TESTING THE DUPLICATING CHARACTERISTICS OF PRESSURE-SENSITIVE DUPLICATING SHEETS

The present invention is directed to a method and an apparatus particularly for testing the duplicating or copying characteristics of pressure-sensitive duplicating sheets or papers such as copying or carbon papers. More particularly, the invention is directed toward testing the intensity, stroke or line sharpness, readability and soiling or smearing tendency of the duplicating sheets or papers and duplicating sets which may be produced therefrom.

In the practice of a method of the type to which the present invention relates, a stroke grid or screen is drawn upon the duplicating paper or duplicating set produced therefrom, respectively, by means of a mechanically or electromechanically actuated marking stylus with a selectable or predetermined contact force and the grid produced is visually evaluated or is evaluated by means of photoelectronic reflectance or reflection measurement.

Some qualitative criteria for pressure-sensitive duplicating papers include, for example, typing intensity, stoke sharpness, readability, soiling tendency and duplicating behavior when used in multiple sets. When evaluating such qualitative criteria, it is necessary to distinguish between the various areas of application distinguished through characteristic duplicating energy areas or ranges and these may include copying by hand, high speed printing copies or typewriter copies.

In any case, there will be involved the transference of type characters such as letters, numerals and the like which are composed of narrow lines and which do not constitute large surface area characters.

In order to judge the type intensity alone, it would generally be sufficient to produce holohedral, i.e., full surface, fully dimensional, copies which may for example be in the form of calendar prints or impressions. Also, holohedral copies are produced, for example, with commercially available proof or testproof devices. In order to judge the type intensity, these holohedral prints have the advantage that the intensity of such prints which may, for example, be a black copy, may be measured over a large surface area reproduction by means of conventional measuring devices such as reflectance photometers so that the photometric evaluation will provide a value integrated over a larger surface, which value will correspond to the perception of the human eye.

A disadvantage of holohedral copies produced in this manner, which are generally produced between rigid plates or rollers, is that the copies which are obtained tend to be uneven or nonuniform inasmuch as things such as uneven paper formations and thicknesses and/or fluctuations in the density or consistency will lead to printing defects or influences which will fluctuate in places. For example, in calendar printing, thinner and/or less dense points between adjacent thicker and/or denser points may be hardly loaded or perhaps not loaded at all so that a lighter point or area will result in the copy. However, this does not correspond to actual conditions in copying individual characters which due to their small surface area dimensioning can also comprehend such areas.

Additionally, if it is desired, aside from the intensity, to obtain information about other qualitative criteria such as stroke sharpness and readability, then individual characters must be written or printed. Commercially available high speed printers or typewriters are often employed for producing characters, such as is described also in the ASTM F 591-78 and ASTM F 497-77. Generally however these are unsuitable for testing purposes because of the unsatisfactory reproducibility of the printing forces. This disadvantage may be avoided by means of expensively constructed laboratory devices which substantially simulate the mechanical printing process.

It has already been attempted with the Fogra printing tester to combine features of the holohedral testing procedure with one wherein individual characters are used. However, in the latter as well the previously described disadvantages of the holohedral method are not eliminated inasmuch as unevenness of paper formation has a disturbing effect and accordingly leads to unsatisfactory reproducibility of results.

Another principle which has been practiced is the so-called Graphic-Kuli device wherein copies are produced with the aid of a circularly moving loaded ball point pen cartridge wherein at least the reproducibility of the force effect is favorably achieved.

One of the most significant disadvantages of individual copies composed of individual type characters is that a most important qualitative criteria, the type intensity, is very difficult to measure. The problem consists in that in an already weaker enlargement the linear type picture or image appears discontinuous since adjacent areas are maybe perceived with and without color reaction. Because of the statistical or random character of these irregularities, strong fluctuations in the photometric signal will result with the consequence that a large number of individual measurements must be averaged for reliable information. Moreover, the micro-photometric picture in no way corresponds to that which would be perceived by the human eye, so as to integrate over a large area.

In previously known methods for testing the duplicating characteristics of pressure-sensitive duplicating papers there has been produced either relatively large holohedral copies or linear copies with known disadvantages. These disadvantages arise in that with the holohedral copies light/dark appearances are created as a result of the anisotropy of the carrier paper caused by fiber distribution, with such light/dark appearances tending to disturb or falsify the measured value during subsequent evaluation. With linear or line copy, the evaluation must be effected, as described above, either photoelectronically in the weakly enlarging microscopic area or range and it is therefore accordingly costly in terms of the apparatus and time or there will be comprehended inscribed as well as uninscribed surfaces as, for example, with the Graphic-Kuli, with the measuring opening of the photometer. Since the portion of white surface is large compared with the inscribed surface, the true type intensity is not measured but rather an intermediate value from inscribed and uninscribed surface which is not capable of delivering information. An objective comparison of the duplicating characteristics of pressure-sensitive duplicating papers is, accordingly, only possible to be achieved in a restricted sense or not at all and thus visual judgment must be used with all the disadvantages and the possibility of subjective error which is involved.

Accordingly, the present invention is directed toward provision of a method and apparatus for testing the duplicating characteristics of pressure-sensitive duplicating papers wherein there is combined the advantages of a holohedral testing procedure with those of a stroke-shaped or punctiform testing procedure without giving rise to their disadvantages.

More particularly, the conditions for production of the copy will correspond to a great extent to the conditions during the duplicating process in actual practice. Moreover, the invention is directed toward enabling the possibility of equally good judgment of the legibility, stroke sharpness and soiling tendency, aside from the optimal and objective judgment of the intensity, wherein the evaluation may be effected without great expenditure of time with commercially available devices of proven practicality such as, for example, reflectance photometers.

SUMMARY OF THE INVENTION

Briefly, the present invention may be described as a method and apparatus for testing the duplicating characteristics of pressure-sensitive duplicating sheets and duplicating sets produced therefrom, and in particular for testing characteristics such as intensity, stroke sharpness, legibility and soiling tendency of the pressure-sensitive duplicating papers or sheets, wherein a stroke grid is drawn upon duplicating paper to be tested by means of a mechanically or electromechanically actuated marking stylus having selectable or predetermined contact force with the grid thus produced being evaluated possibly by means of photoelectronic reflectance measurement, the individual strokes of the stroke grid which is applied to the duplicating paper consisting essentially of individual strokes which overlap or are closely adjacent to one another without intersecting.

With the method in accordance with the present invention, the disadvantages of previously known testing techniques are overcome and thus there may be avoided disadvantages such as uneven or nonuniform hollow holohedral copies, the requirement for evaluation of individual copies in the microscopic area or range, poorly reproducible measuring results and qualitative criteria which can only be subjectively judged such as, for example, the legibility of the copy.

A testing method is thus provided which, in addition to its ease of measurement, provides objective criteria which can be reproduced as often as is desired in order to enable the evaluation of the qualitative characteristics of the duplicating papers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DETAILED DESCRIPTION OF THE PREFERRED EMBODIMENTS

Figure 1:
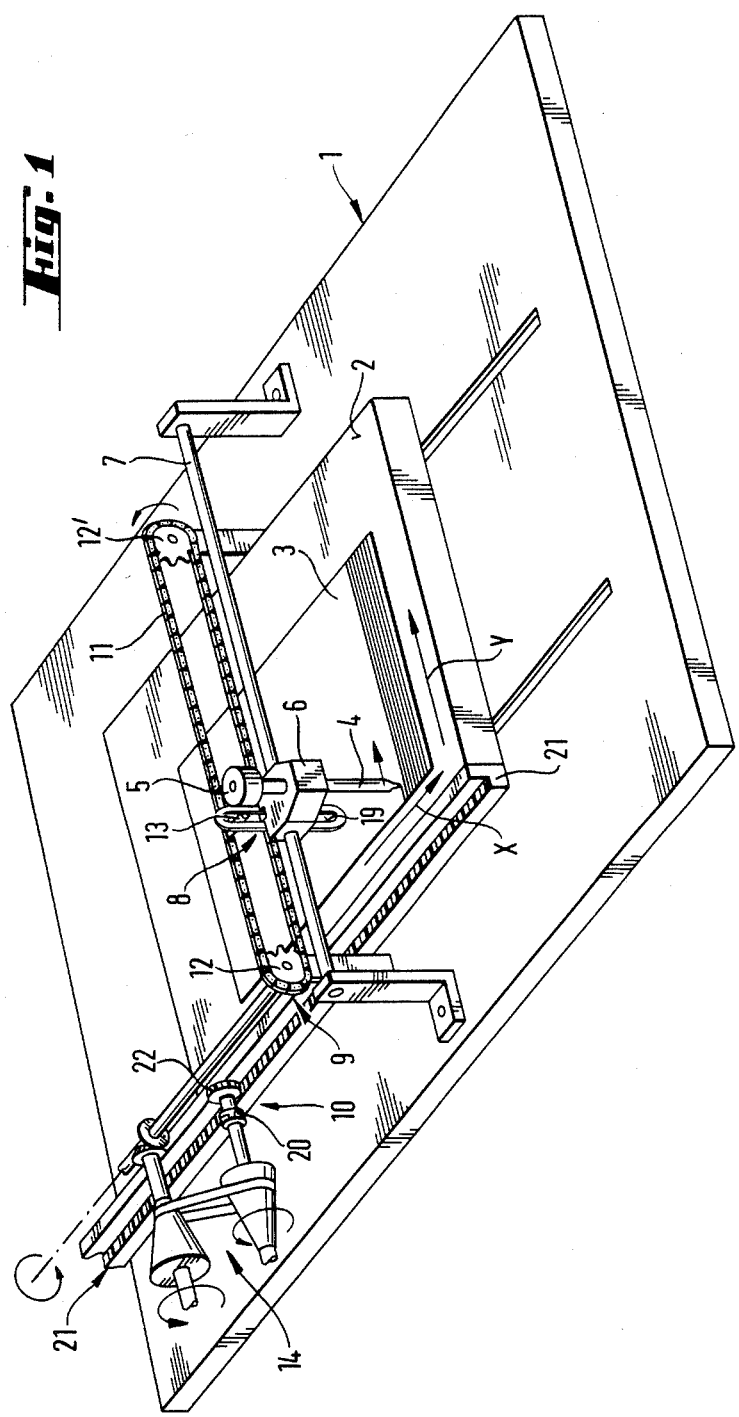
FIG. 1 is a perspective view showing a preferred embodiment of a mechanical device for carrying out the method according to the invention.

Referring now to FIG. 1, there is shown a preferred embodiment of a mechanical device for practicing the method of the present invention. The embodiment shown in FIG. 1 comprises a base plate 1 having thereon a contact plate 2 upon which there is supported a duplicating set 3 which comprises the duplicating sheets or papers to be tested. The contact plate 2 is attached on the base plate 1 and is guided for movement in a direction X.

The apparatus further comprise a marking stylus 4 which has provided thereon additional weights 5 for applying a load to the marking stylus 4 in order to enable determination of the force or pressure with which the marking stylus 4 contacts the duplicating set 3.

The marking stylus 4 is itself articulated at a linear guide 7 by means of a holder 6. The linear guide 7 is, in turn, connected with the base plate 1 by means of a pair of perpendicular or vertical support members. The holder 6 has thereon a carrier 8 which is connected in operative engagement with a coupling gear unit 9 which operates to effect movement of the holder 6 together with the marking stylus 4 guided therein in a direction Y.

The coupling gear unit 9 comprises an endless roller chain 11 which is guided about a pair of wheels 12 and 12'. A mandrel 13 is fastened at the roller chain 11 and engages within a slot 19 located in the carrier 8. As a result of movement of the mandrel 13 by the endless chain 11 and due to its engagement within the slot 19, the mandrel 13 effects reciprocating lateral movement of the marking stylus 4.

The device also comprises a change gear unit 14 which operates to drive the contact plate 2 in the X direction and which also operates to rotate the wheel 12 in order to drive the endless chain 11. As will be noted, the change gear unit 14 is connected by a bevel gear set with the wheel 12 to rotate the wheel 12 as indicated by circular arrow in FIG. 1. Additionally, the change gear unit 14 includes a spur gear 22 which engages a rack 21 on the contact plate 2 in order thereby to drive the contact plate 2 in the X direction. The change gear unit 14 operates to effect forward feed of the contact plate 2 through a coupling gear unit 10 which consists of a stepping mechanism 20 so that the desired forward feed of the contact plate 2 in the X direction is effected in such a manner that during each return movement of the marking stylus 4, the contact plate 2 is displaced in the X direction by a preselected distance as a result of operation of the gear unit 10.

Another advantageous embodiment of the invention for effecting the method of the invention is one which consists of an electromechanically or electrically actuated device which may be composed of a commercially available Y-t recorder with a registering or recording stylus and an electrical transmitter wherein the latter consists of a commercially available frequency generator which produces the required electrical signals for actuation of the marking stylus which is movable in the Y direction. The transmitter is connected with the input terminals of the recorder so as to be electrically conducting. Instead of the pen of the recorder, the marking stylus is articulated at the movement device by means of a holder so as to be movable so that the marking stylus may follow the Y components and will also be freely movable in the vertical or Z direction. It has been shown to be advisable to replace the originally existing pen holder with a mechanically reinforced holder capable of ensuring a secure guidance of the marking stylus and of transferring the required acceleration forces to the marking stylus loaded with weights. In the case of a Y-t recorder, this forward feed will be already integrated structurally in commercially available devices in the form of the recording paper forward feed. It has proven useful to have several forward feed speeds available.

Of particular advantage in carrying out the method of the invention is an X-Y recorder connected with an electrical transmitter. In such apparatus, the marking stylus is moved over the duplicating paper or the duplicating set produced from the duplicating paper, in the X and Y directions while the duplicating paper to be tested is fixedly attached on a stationary contact plate of the recorder. Movement of the marking stylus is, in turn, effected by the electrical transmitter by means of electrical signals wherein the transmitter has two signal outputs, one of which controls or guides the Y components while the other controls the X components of the recorder. The electrical signals required for actuation of the marking stylus in the Y direction are produced by an electrical transmitter in the form of triangular, rectangular or sinusoidal signals as variable voltages U or as variable amperage current I. All three signal forms have shown in principle to be effective but it is considered most advantageous to select the triangular signal since in this signal shape the electromechanical drive for movement of the marking stylus is only slightly mechanically loaded due to acceleration forces which are applied. For movement of the marking stylus in the X direction, a linearly or stepwise increasing signal is produced by the electrical transmitter in the form of a voltage U or a current of amperage I. A linear signal effects a constant movement and a step-shaped or graduated signal a stepwise movement of the marking stylus in the X direction.

Figure 2:
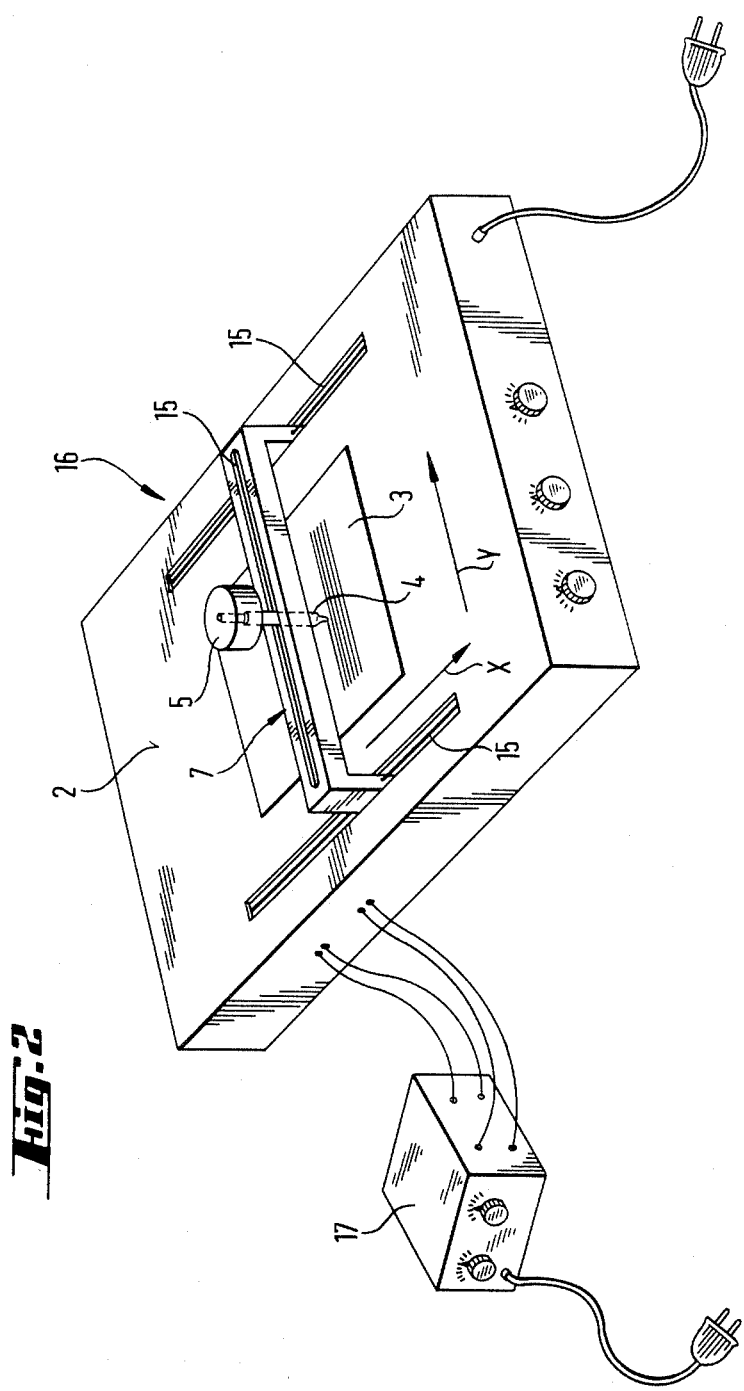
FIG. 2 is a perspective view showing electrical apparatus for carrying out the method of the invention.

In FIG. 2 there is depicted an electrical apparatus for carrying out the method of the invention which comprises a second embodiment of the invention. In the embodiment shown in FIG. 2, there is provided an electrical transmitter 17 which is supplied with current from a current source (not shown) and which produces signals for movement in the X and Y directions and which feeds these signals into an electrical recorder 16 by means of electrical cable connections. A duplicating set 3 to be tested is affixed or fastened on the contact plate 2 of the electrical recorder 16. The linear guide 7 moves over the duplicating set 3 in the X direction with a marking stylus 4 oscillating in the Y direction, the marking stylus 4 being loaded by the additional weights 5 and in so doing producing the desired stroke grid.

The strokes which are applied to the duplicating paper in accordance with the embodiments of the invention will overlap or will be closely adjacent to one another but do not intersect and are representative of individual surfaces having a finite width whose dimensions are determined by the tip of the marking stylus. The distance of the individual strokes from one another is defined as the distance of the individual stroke centers relative to one another. If the distance is preferably selected in such a manner that a stroke grid results whose individual strokes can no longer be resolved by the human eye, a holohedral results. As a result of this, the copies, which consist of individual strokes but which appear to the human eye as a holohedral, are advisably produced by means of an oscillating movement of a loaded marking stylus with simultaneous forward feed of the duplicating paper to be tested wherein paper/marking stylus forward feed and frequency of the marking stylus are adapted or matched to one another. There is thus obtained holohedral copies of the desired size which are characterized by extraordinary uniformity. The anisotropy of the carrier paper is not a problem. Spotted holohedral copies do not occur as would be obtained for example with copies which are printed, impressed or reproduced between rigid rollers or plates. It is advisable if the distance of the individual stroke centers is, additionally, selected in such a manner that it would amount to 30 to 150% of the stroke widths. The individual strokes which form the stroke grid extend parallel or at an acute angle relative to each other. Both types of arrangements have been shown to be effective. If the strokes extend at an acute angle relative to each other, that is if the writing trace of the marking stylus is a zigzag line, then the distance of the stroke centers in the center between two return stationary points of the zigzag line must be fixed at between 30 and 150% of the stroke width.

A holohedral which is sufficient for electrical reflectance measurement can be obtained in that the distance of the individual stroke centers relative to one another will amount to 30 to 150% of the stroke width. The length and width of the holohedral produced in this way will remain open at first and it is only dependent on the diameter of the measuring opening of the reflectance photometer. It is advisable if the width of the holohedral to be produced is selected in such a way that it is somewhat larger than the measuring opening. The length of the holohedral is advisably selected in such a manner that it is a multiple of the diameter of the measuring opening. There may accordingly be obtained several adjacent measuring surfaces for the measurement. If, for example, the diameter of the measuring opening of the photometer is 30 mm, then the length of 90 mm is selected for the holohedral to be produced. There may accordingly be obtained three separate measuring surfaces.

In order to adjust or reset the various printing or pressure forces of the writing pressures which occur in practice, such as would occur with hand copying, high-speed printers and typewriters, in order to be reproducible during production of the holohedral copies, the marking stylus is guided over the duplicating paper to be written upon or over the duplicating set produced therefrom with a vertical or perpendicular contact force of between 0.1 to 5.0 N. In order to evaluate the intensity, the copied holohedrals are referred to the copies of the duplicating set. If the duplicating set consists of so-called single layer paper (self contained paper) the holohedral can also be used for measurement on the cover sheet of the duplicating set.

The type intensity of holohedral copies produced in this way may be very simply measured by determining the brightness difference $\Delta y$ between inscribed and uninscribed surfaces or the intensity can be given as a quotient of the difference of the brightness $\Delta y$ and the brightness y of the uninscribed surface in percentages. With the described method, a reproducible intensity value is obtained for a determined type of duplicating paper. If the contact force of the marking stylus is varied within the range of between 0.1 to 5.0 N when producing the copies, then in the case of multiple sets a curve is obtained for each copy when the photometrically measured type intensities are plotted against the contact force. These curve groups are to be viewed in practice in fingerprints for a duplicating paper with certain qualitative characteristics. If the curve groups are extrapolated to low contact forces, then the soiling susceptibility of the duplicating paper is simultaneously characterized. There occurs a technical concern in determining the soiling susceptibility because by means of unintentional, slight applications of pressure and impacts occurring when the paper is in use, such undesired soiling can occur which is greater with more sensitive paper which tends to discolor at low pressures.

The legibility of copy produced with a duplicating paper depends upon the intensity and the stroke sharpness of the produced and copied character or sign. A high intensity in connection with good stroke sharpness means good legibility, a low intensity and poor stroke sharpness means poor legibility. The stroke sharpness that can be achieved with a certain duplicating paper is chiefly determined by the base or raw paper quality and the characteristics of the coating applied thereon during the printing or pressure effect caused by the inscribing means. If it is desired to measure the stroke sharpness which is achievable with a duplicating paper, the individual strokes must be arranged in such a manner that the distance or spacing of the individual stroke centers will amount to 100 to 150% of the stroke width. Because of the print ball, which is built up or formed by the writing or marking stylus in the duplicating set to be tested, the strokes which are still capable of being perceived on the cover sheet of the duplicating set as individual strokes will widen increasingly and finally overlap in the following sheets of the set so that conclusions may be drawn regarding the influence of stroke sharpness by the paper to be tested. If, instead of a grid with strokes extending parallel relative to each other, there is selected a grid with strokes which extend at acute angles relative to each other for judging the stroke sharpness, whose distance from one another likewise amounts to between 100 and 150% of the stroke width, then the evaluation is effected in such a manner that the surfaces in the wedges or gussets that are formed by means of the strokes extending at acute angles relative to one another are judged. By wedges or gussets there is meant a triangular surface area, for example, between an arc and its rectangular frame.

In effecting the method of the invention with the apparatus previously described, the marking stylus which is movable in the Y direction can be preferably loaded with exchangeable additional weights in order to achieve contact forces of, for example, between 0.1 N to 5.1 N in stages or degrees of 0.5 N. Any type of stylus may be used as the marking stylus but it has been shown to be preferable to employ only such styli whose tips ensure a punctiform contact with the paper surface wherein the tip is exposed to only minimum wear or no wear at all and wherein the tip glides with a rolling friction over the paper to be tested. Ball point pen cartridges according to DIN (German Industrial Standards) such as for example Pelikan Perfekt 237M, have proven particularly desirable for this purpose. The marking stylus is vertically movably guided in a holder so that it can glide without friction under the influence of the weights which can be placed on the end remote of the writing stylus. The holder is articulated at a linear guide and may be moved in the Y direction along this linear guide over the contact plate with the duplicating set located thereon. The first coupling gear unit or linkage is used for the oscillating movement of the holder which is connected with the marking stylus along the linear guide. In principle, known mechanical gear units capable of converting a constant rotational movement into linear movement may be utilized as coupling gear units. For example, there may be utilized crank gear units, eccentric gear units, control roller gear units, tie rod pull band or pull chain gear units.

The stroke or lift length, as well as the speed of the linear movement of the marking stylus is produced by means of the first coupling gear unit. If the stroke length and/or speed of the linear movement of the marking stylus is to be changed in the Y direction, this may be effected by means of changing the crank radius or the control roller geometry or the number of revolutions of the tie rod or chain gear unit as well as by means of lengthening the shortening the tie rod. For the forward feed of the contact plate in the X direction, a second coupling gear unit is connected with the latter in an interlocked manner. For this purpose, the contact plate is provided with devices such as toothed racks, openings, ets. The second coupling gear unit is equipped with a device for changing output speed. This is preferably formed from changeable or replaceable gear wheels or wheel transmissions in order to enable adjustment of the linear forward feed speed of the contact plate in the X direction in the desired areas or ranges. If a stepwise forward feed of the contact plate in the X direction is desired, the second coupling gear unit is preferably structured as a stepping mechanism which may comprise for example a pawl or ratchet drive or a Maltese cross or Geneva stop drive. It has been found to be particularly preferable to connect the first and second coupling gear units with one another in an interlocked manner since it may thereby be ensured that the movements produced by the two gear units will always be in a constant relationship relative to each other and may operate to provide reproducible stroke grids.

It will thus be seen from the foregoing that the invention provides a method and apparatus for testing duplicating characteristics of pressure-sensitive duplicating paper and duplicating sets produced therefrom wherein a stroke grid is drawn upon the duplicating paper, or upon duplicating sets produced therefrom, by means of a mechanically or electromechanically actuated marking stylus capable of operating with preselected or predetermined contact force and the grid produced is visually evaluated or evaluated by means of photoelectric reflectance measurement. The stroke grid which is drawn consists of individual strokes which overlap or are closely adjacent but do not intersect. In this manner, holohedral copies of the desired size are obtained which are distinguished by extreme uniformity and their contrast to the uninscribed surface of the duplicating paper can be evaluated with commercially available photoelectric reflectance measurement devices.

The apparatus for carrying out the method consists of a contact plate for the duplicating set to be tested which contact plate is movable in the X direction with a marking stylus being provided which is movable in the Y direction and to which varying contact forces can be applied.

As previously indicated, the individual strokes which are applied are applied in such a manner that the distance between individual stroke centers relative to each other is between 30 to 150% of the stroke width.

The coupling gear unit 9 may be arranged or structured so that the stroke length and/or the output speed of the coupling gear unit 9 may be adjustable. Also, the output speed of the coupling gear unit 10 may also be adjustable.

As will be seen from FIG. 1, the first coupling gear unit 9 is connected with the second coupling gear unit 10 in an interlocking manner by means of the mechanical change gear unit 14.

Furthermore, in accordance with the embodiment of FIG. 2, a transmitter producing electrical signals is coupled with drive aggregates for movement in the Y and/or X directions.

While specific embodiments of the invention have been shown and described in detail to illustrate the application of the inventive principles, it will be understood that the invention may be embodied otherwise without departing from such principles.

What is claimed is:

1. A method for testing the duplicating characteristics of pressure-sensitive duplicating sheets and duplicating sets produced therefrom comprising the steps of drawing a stroke grid on said duplicating sheets by means of a marking stylus, said stylus being actuated by one of a mechanical and electromechanical mechanism to apply a selective contact force to said sheets, and evaluating said grid thus produced, said stroke grid consisting essentially of a plurality of individual strokes which are at least closely adjacent but which do not intersect wherein said individual strokes overlap.

2. The method according to claim 1 wherein said individual strokes are applied so as to extend parallel relative to each other.

3. A method for testing the duplicating characteristics of pressure-sensitive duplicating sheets and duplicating sets produced therefrom comprising the steps of drawing a stroke grid on said duplicating sheets by means of a marking stylus, said stylus being actuated by one of a mechanical and electromechanical mechanism to apply a selective contact force to said sheets, and evaluating said grid thus produced, said stroke grid consisting essentially of a plurality of individual strokes which are at least closely adjacent but which do not intersect, said individual strokes being applied in such a manner that the distance of the individual stroke centers relative to each other is in the range of between 30 to 150% of the stroke width.

4. The method according to claim 3, wherein said individual strokes are applied so as to extend parallel relative to each other.

5. The method according to claim 3, wherein said individual strokes are applied in such a manner that they extend at acute angles relative to each other.

6. Apparatus for testing the duplicating characteristics of pressure-sensitive duplicating sheets and duplicating sets produced therefrom comprising a contact plate for supporting thereon said duplicating sheets to be tested, means for moving said marking stylus and said contact plate relative to each other in two directions perpendicular to each other, means for controlling the contact force which is applied by said marking stylus on said duplicating sheets, means for controlling the movement of said contact plate and said marking stylus relative to each other for drawing a stroke grid on said duplicating sheets, said marking stylus and said contact plate being controlled so that said stroke grid consists essentially of a plurality of individual strokes which are at least closely adjacent but do not intersect.

7. Apparatus according to claim 6 wherein said contact plate and said duplicating sheets mounted thereon are held in a fixed position and wherein said marking stylus is movable relative thereto in a first direction and in a second direction perpendicular to said first direction.

8. Apparatus according to claim 6 further comprising linear guide means having said marking stylus movably articulated thereon, said linear guide means including a holder for said marking stylus.

9. Apparatus according to claim 6 further comprising first coupling gear unit means for effecting oscillating movement of said marking stylus in a first direction and second coupling gear unit means for effecting forward feed of one of said contact plate and said marking stylus in a second direction perpendicular to said first direction.

10. Apparatus according to claim 9 wherein at least one of the stroke length and the output speed of said first coupling gear unit means is adjustable.

11. Apparatus according to claim 9 wherein the output speed of said second coupling gear unit means is adjustable.

12. Apparatus according to claim 9 wherein said second coupling gear unit means comprises a stepping mechanism.

13. Apparatus according to claim 9 wherein said first coupling gear unit means is connected with said second coupling gear unit means in an interlocking manner by means of a mechanical change gear unit means.

14. Apparatus according to claim 6 comprising transmitter means for producing electrical signals coupled with drive aggregates for movement in said first and said second directions.

* * * * *